US006402696B1

United States Patent
Nitzan et al.

(10) Patent No.: US 6,402,696 B1
(45) Date of Patent: Jun. 11, 2002

(54) METHOD FOR SYSTOLIC BLOOD PRESSURE MEASUREMENT

(75) Inventors: Meir Nitzan, Beit El; Chaim Rosenfeld; Anatoly Babchenko, both of Jerusalem, all of (IL)

(73) Assignee: Ninbar Ltd., Jerusalem (IL)

( * ) Notice: Subject to any disclaimer, the term of this patent is extended or adjusted under 35 U.S.C. 154(b) by 0 days.

(21) Appl. No.: 09/545,190

(22) Filed: Apr. 7, 2000

(51) Int. Cl.[7] .............................................. A61B 5/02
(52) U.S. Cl. .................... 600/494; 600/485; 600/490; 600/496
(58) Field of Search .................. 600/481, 485–486, 600/490, 493–495, 500, 504

(56) References Cited

U.S. PATENT DOCUMENTS

| | | | | |
|---|---|---|---|---|
| 4,832,039 A | * | 5/1989 | Perry et al. ................. | 600/493 |
| 5,218,967 A | * | 6/1993 | Shinomiya et al. ..... | 600/494 X |
| 5,730,139 A | * | 3/1998 | Miyazaki et al. ........ | 600/494 X |
| 5,746,698 A | * | 5/1998 | Bos et al. .................... | 600/493 |
| 5,862,805 A | * | 1/1999 | Nitzan ..................... | 600/479 X |
| 6,120,459 A | * | 9/2000 | Nitzan et al. ............... | 600/493 |

* cited by examiner

*Primary Examiner*—Robert L. Nasser
(74) *Attorney, Agent, or Firm*—Mark M. Friedman

(57) ABSTRACT

A method for measuring systolic blood pressure includes raising the cuff pressure in such a manner that two conditions are satisfied: (1) The cuff air pressure takes sufficient time to reach the SBP value to avoid blood pressure in the arteries under the PPG sensor being too low, thereby avoiding collapse of the arterioles under the PPG sensor; and (2) The increase of the cuff air pressure between the DBP value and the SBP value is not overly slow in a manner which would cause a relatively high mean blood pressure in the arteries distal to the cuff, and could lead to reduced sensitivity in detecting the restart of blood flow when the cuff air pressure decreases to just below SBP value.

19 Claims, 5 Drawing Sheets

FIG. 4B (EXAMPLES 1-3)

METHOD FOR SYSTOLIC BLOOD PRESSURE MEASUREMENT

FIELD AND BACKGROUND OF THE INVENTION

The present invention relates to measurement of systolic blood pressure and, in particular, it concerns a method for measuring systolic blood pressure using photoplethysmographic (PPG) sensors.

General Background

The assessment of the systolic and the diastolic arterial blood pressure has both physiological and clinical significance, and tremendous efforts have been applied to the development of a reliable noninvasive method for their measurement. Manual sphygmomanometry, which is based on an external cuff and audible detection of Korotkoff sounds, is considered to be the most accurate method, to which other methods should be compared, though it is prone to several sources of error. These include insufficient hearing acuity of the user, the auscultatory gap, and behavioral factors which influence the level of blood pressure, such as the presence of a physician. These errors are avoided when automatic measurement of the blood pressure is performed, but the available automatic noninvasive blood pressure (NIBP) meters and monitors have other sources of error, significantly reducing their accuracy.

Several methods have been suggested for automatic NIBP measurement. The most widely used of these, together accounting for about 96% of all NIBP monitors currently in use, are oscillometry and the auscultatory method. Oscillometry is based on the measurement of the change in the cardiac induced air pressure oscillations in the pressure cuff during cuff deflation after the elevation of the cuff air pressure above the systolic blood pressure. The cuff pressure at which the oscillometric pulse amplitude is maximal is generally regarded as the mean arterial pressure (MAP). The systolic (SBP) and the diastolic (DBP) blood pressures are determined from the envelope of the oscillometric curve using empirical criteria, such as the cuff pressure of maximal (or minimal) slope or of a determined value of the amplitude relative to maximal amplitude. These empirical criteria are the main source of error in oscillometry since they depend on the character of the cuff and since they are not appropriate for all patients. The automatic auscultatory method is also prone to artifacts due to external noise and vibrations.

The accuracy of the available automatic NIBP meters is very low, as can be understood from the standards imposed by the Association for the Advancement of Medical Instrumentation (AAMI) and the British Hypertension Society (BHS). Both standards are based on comparing the automated NIBP meter to manual sphygmomanometry (which is taken as a "gold standard") for at least 85 subjects. The standards require that the mean difference between the SBP (or DBP) values measured by the sphygmomanometer and the device under examination do not exceed 5 mmHg, and that the standard deviation of that difference should not exceed 8 mmHg. In other words, a device for which 37% of the examinations differ from the reference manual sphygmomanometer by more than 8 mmHg and 5% of the examinations differ from the reference device by more than 16 mmHg is acceptable. Such low accuracy is permitted because the known methods are not capable of providing measurements of higher accuracy.

PPG-Based Techniques

Both the auscultation method and oscillometry are based upon indirect physiological effects such as Korotkoff sounds, whose origin is not clear, or upon empirical parameters of the oscillometric envelope curve.

The volume-oscillometric method, like the oscillometric method, is based on the measurement of the arterial blood volume oscillation changes as a function of the pressure of an external cuff placed over the artery. The difference between the two methods is that in oscillometry the arterial volume oscillations are measured by means of pressure oscillations in the cuff itself, while in volume-oscillometry these oscillations are measured by photoplethysmography (PPG) or by another plethysmographic device placed under the cuff. As a result, in contrast to oscillometry, no oscillations are detected by the volume-oscillometry sensor, which is located at the distal end of the cuff, when the cuff pressure is above the systolic blood pressure. (In oscillometry the pressure in the cuff continues to oscillate even in high cuff pressure due to the impact of the arterial blood on the tissue under the proximal end of the cuff). Hence, volume oscillometry enables the measurement of systolic blood pressure more directly than oscillometry, with no need for empirical formula.

Systolic Blood Pressure Measurement By PPG

In principle, the measurement of systolic blood pressure using a pressure cuff and a PPG sensor is very straightforward. At cuff pressures below the SBP, some blood passes through the arteries under the cuff, producing pulsatile tissue blood volume variations which generate pulses in the PPG signal. Above the SBP, the artery under the cuff collapses, resulting in interruption of the pulsatile blood volume variations. FIG. 1 illustrates schematically a system for the measurement of the SBP using a pressure cuff 1 and a PPG sensor 2. A mercury manometer 3 is typically provided for calibration, while primary measurement and control of pressure in the cuff are performed, respectively, by a piezoelectric transducer 4 and a pressure pump (and its electronic control) 5. These cuff control components, as well as the electronic control 6 of the PPG device are all connected via an A/D card to a computer 7 which analyzes the results.

FIG. 2 shows typical curves of the PPG signal and of the air pressure as a function of time during the decrease in the cuff air pressure. Note the start of the PPG pulses when the air pressure decreases below SBP value.

Although theoretically simple, the actual measurement of SBP by this technique presents significant problems. Firstly, the amplitude of the first PPG pulses immediately after the air pressure falls below the SBP is small, often making it difficult to identify reliably from background noise in the PPG signal. More importantly, it has been found that, in 15–20% of subjects, no pulses are actually detected in the PPG signal until the pressure has decreased beyond the actual SBP (measured by Korotkoff sounds) by as much as 10–20 mmHg. Without in any way limiting the scope of the present invention, this latter problem is believed to be attributable to the mechanical pressure applied by the PPG sensor itself on the arteries underneath. When the cuff air pressure is above SBP, the arteries distal to the cuff drain into the veins so that the arterial blood pressure becomes relatively low and the small pressure exerted by the sensor can make them collapse (close them). In some cases the small blood volume pulses entering the arteries distal to the cuff when the cuff air pressure is just below SBP value cannot open the arteries under the sensor.

Finally, reference is made to U.S. Pat. No. 5,447,161 to Blazek et al. which proposes a method for measuring venous blood pressure, SBP and DBP during a slow increase (4 mmHg/s) in applied cuff pressure. When the applied external pressure is above the venous blood pressure, the veins collapse. As a result, the slow air pressure increase leads to accumulation of much blood in the hand vascular system. As will be detailed below, the slow increase leads to reduction in the distal PPG signal amplitude so that the PPG signal may initially be undetectable when the cuff air pressure decreases to slightly below the SBP. This renders SBP measurement unreliable.

There is therefore a need for a method for measuring arterial systolic blood pressure using a cuff and a PPG sensor which would provide accurate and reliable results.

SUMMARY OF THE INVENTION

The present invention is a method for measuring arterial systolic blood pressure in a subject.

Conceptually, the present invention provides two approaches to overcoming the problem of delayed PPG sensing of cardiac induced pulsatile variations in tissue blood volume just below the systolic blood pressure.

According to a first, particularly simple approach, the form of attachment of the PPG sensor is modified to minimize pressure exerted on the adjacent tissue. Thus, according to one preferred implementation, a PPG sensor is attached to the fingernail of a subject, typically by use of double-sided, transparent adhesive tape. The contact surface of the PPG sensor is modified to provide a curvature approximating to that of a typical fingernail. In other respects, the PPG sensor is a conventional sensor of either the transmission type or of the reflection type.

Although this first approach has been found to provide very accurate and reliable SBP measurements under controlled conditions, it is thought that the lack of significant contact pressure would lead to problems of signal instability in cases where the subject does not remain still. This is particularly true for applications with significant motion such as during stress tests or when the patient is being transferred by ambulance.

To avoid these practical limitations, the present invention also provides a second approach which is believed to be suitable for a wider range of applications and to provide highly accurate and reliable SBP measurements. According to this second approach, the cuff pressure increase before it reaches SBP value is performed in such a manner as to cause venous occlusion for a period of time, long enough to sufficiently increasing venous blood volume and pressure. The latter prevents the drainage of the arteries of their blood, so that the arteries remain open even under the mechanical pressure of the PPG sensor. This has been found to avoid the problem of failure to detect the PPG pulses at pressures just below the SBP.

According to the aforementioned approach, the cuff air pressure increase should last for long enough period of time in order to prevent emptying of the arteries after the closure of the arteries under the cuff. If the cuff air pressure increases slowly up to the value of DBP or lower, and then increases fast to above SBP value, no significant change in the blood pressure in the distal arteries is expected. If, however, the cuff air pressure slowly increases above the DBP value, the mean arterial blood pressure will increase. By way of illustration, when the cuff air pressure is above DBP, say 100 mmHg (for a subject whose SBP/DBP values are 120/80 mmHg), the artery under the cuff opens during the part of the systole for which the arterial blood pressure is above 100 mmHg, and blood enters the arteries distal to the cuff. During diastole, if the arterial blood pressure distal to the cuff remains above 100 mmHg, blood drains back from these arteries through the cuff. When the arterial blood pressure is below 100 mmHg, the artery under the cuff collapses, so that the blood pressure in the arteries distal to the cuff is remains at least 100 mmHg. This occurs if the increase of the cuff air pressure is slow enough.

Hence, the manner of increasing pressure in the cuff should be so chosen to prevent the mean blood pressure approaching the systolic blood pressure, in order to avoid the problem of reduced amplitude of PPG pulses due to distended blood vessels. For higher blood pressure, the arteries walls are more distended and their compliance (the increase of the arterial blood volume for a given increase of blood pressure) is low. By way of illustration, FIG. 3 shows the relationship between the volume of the arteries and their transmural blood pressure, i.e. the difference between the arterial blood pressure and the external pressure. It can be seen that blood volume increase due to a given blood pressure increase is smaller for higher blood pressure. As a result, when the cuff air pressure decreases to slightly below the SBP (after slow increase of the cuff air pressure which causes the mean arterial blood pressure to be relatively high), the small changes in arterial blood pressure will result in very small changes in the arterial blood volume such that the pulses in the PPG signal may be masked by the existing background noise.

The aforementioned U.S. Pat. No. 5,447,161 to Blazek et al. suffers from exactly this problem. Because of the slow increase (4 mmHg/s) in the applied cuff pressure, much blood accumulates in the hand and arm vascular system, so that the mean blood pressure approaches the systolic blood pressure and blood flow into the arteries distal to the cuff is greatly reduced. This presents problems for the SBP measurement which is performed by detecting the start of blood flow when the cuff air pressure decreases below SBP value. By way of illustration, we performed tests in which we measured the systolic blood pressure by the auscultatory method for a set of 19 subjects using fast increase and slow increase of air pressure. The measurement was performed during the subsequent slow decrease of the cuff air pressure. Out of the 19 subjects, the SBP value obtained after the slow increase for 18 of them was lower than that obtained after the fast air pressure increase. This illustrates clearly that, after slow increase of the cuff air pressure of the type proposed by Blazek et al., the blood flow through the artery under the cuff can be detected only when the cuff air pressure has already been lowered significantly below the SBP value.

Because of the more general applicability of this second approach, it is this approach which will form the basis of the various implementations which will be detailed in the following description.

Hence, according to the teachings of the present invention there is provided, a method for measuring systolic blood pressure in a subject, the method comprising: (a) generating a first signal indicative of cardiac induced pulsatile variations in tissue blood volume in a first region of the subject's body; (b) applying a pressure cuff to a second region of the subject's body proximal with respect to the first region; (c) increasing a pressure within the pressure cuff to a pressure sufficient to prevent sensing of cardiac induced pulsatile variations in tissue blood volume in the first region; (d) reducing a pressure within the pressure cuff; and (e) identifying as a systolic blood pressure of the subject a cuff pressure at which the cardiac induced pulsatile variations in tissue blood volume in the first region are found to restart, wherein the increasing of pressure within the pressure cuff is performed such that it takes at least 10 seconds for the cuff pressure to reach 100 mmHg, and such that the average rate of increase is at least 20 mmHg per second from 100 mmHg up to the pressure sufficient to prevent sensing of cardiac induced pulsatile variations.

According to a further feature of the present invention, the identifying includes: (a) integrating the first signal with respect to time over the length of a suspected pulse to derive an area under the pulse; and (b) identifying the suspected pulse as a restarting of cardiac induced pulsatile variations in tissue blood volume only if the area exceeds a given minimum value.

According to a further feature of the present invention, the identifying includes: (a) deriving a maximum gradient of the first signal with respect to time over the length of a suspected pulse; and (b) identifying the suspected pulse as a restarting of cardiac induced pulsatile variations in tissue blood volume only if the maximum gradient exceeds a given minimum value.

According to a further feature of the present invention, the method further includes: (a) generating a second signal indicative of cardiac induced pulsatile variations in a third region of the subject's body; (b) calculating a delay between features of the first and the second signals indicative of corresponding cardiac induced pulsatile variations; and (c) evaluating a baseline value of the delay when the pressure within the pressure cuff is substantially zero, and calculating a corrected delay by deduction of the baseline value from measurements of the delay, wherein the identifying includes identifying a suspected pulse as a restarting of cardiac induced pulsatile variations in tissue blood volume only if the value of the delay is between 100–250 ms.

According to a further feature of the present invention, the method also includes: (a) generating a second signal indicative of cardiac induced pulsatile variations; (b) deriving empirically an approximate relationship between values of a delay of the first signal after the second signal and the cuff pressure; and (c) identifying a suspected pulse as a restarting of cardiac induced pulsatile variations in tissue blood volume only if the suspected pulse occurs within a given time window after a pulse of the second signal, the given time window being derived from the approximate relationship evaluated at an expected value of systolic blood pressure.

There is also provided according to the teachings of the present invention, a method for measuring systolic blood pressure in a subject, the method comprising: (a) generating a first signal indicative of cardiac induced pulsatile variations in tissue blood volume in a first region of the subject's body; (b) applying a pressure cuff to a second region of the subject's body proximal with respect to the first region; (c) increasing a pressure within the pressure cuff to a pressure sufficient to prevent sensing of cardiac induced pulsatile variations in tissue blood volume in the first region; (d) reducing a pressure within the pressure cuff, and (e) identifying as a systolic blood pressure of the subject a cuff pressure at which the cardiac induced pulsatile variations in tissue blood volume in the first region are found to restart, wherein the increasing of pressure within the pressure cuff is performed at a substantially constant rate chosen such that it takes at least between 10 and 30 seconds for the cuff pressure to reach 160 mmHg.

There is also provided according to the teachings of the present invention, a method for measuring systolic blood pressure in a subject, the method comprising: (a) generating first and second signals indicative, respectively, of cardiac induced pulsatile variations in tissue blood volume in a first region and a second region of the subject's body; (b) processing the first and second signals to derive values of a delay between pulses in the first signal and corresponding pulses in the second signal; (c) applying a variable pressure to a third region of the subject's body proximal with respect to the first region so as to affect blood flow through at least one artery in the third region, the variable pressure being varied as a function of time, the first, the second and the third regions being chosen such that the delay varies as a function of the variable pressure; (d) raising the variable pressure at a rate which changes as a function of the delay until the first signal no longer provides identifiable pulses corresponding to cardiac induced pulsatile variations in tissue blood volume; and (e) identifying as the arterial systolic blood pressure the value of the variable pressure corresponding to a boundary below which the first signal includes identifiable pulses corresponding to cardiac induced pulsatile variations in tissue blood volume.

According to a further feature of the present invention, a baseline value of the delay is evaluated when the variable pressure is substantially zero, and a corrected delay is calculated by deduction of the baseline value from measurements of the delay.

According to a further feature of the present invention, the rate is approximately 2 mmHg per second at least for values of the corrected delay below about 50 ms.

According to a further feature of the present invention, the rate is at least about 5 mmHg per second at least for values of the corrected delay between about 50 and about 100 ms.

According to a further feature of the present invention, the rate is approximately 2 mmHg per second at least for values of the corrected delay in excess of about 100 ms.

According to a further feature of the present invention, the boundary is identified during the raising of the variable pressure.

According to an alternative feature of the present invention, the boundary is identified during a subsequent step of reducing the variable pressure.

BRIEF DESCRIPTION OF THE DRAWINGS

The invention is herein described, by way of example only, with reference to the accompanying drawings, wherein:

FIG. 4B is a plot of cuff pressure against time illustrating three examples of preferred sequences of cuff pressure increase according to the teachings of the present invention;

DESCRIPTION OF THE PREFERRED EMBODIMENTS

The present invention is a method for measuring arterial systolic blood pressure in a subject.

The principles and operation of methods according to the present invention may be better understood with reference to the drawings and the accompanying description.

Figure 1:
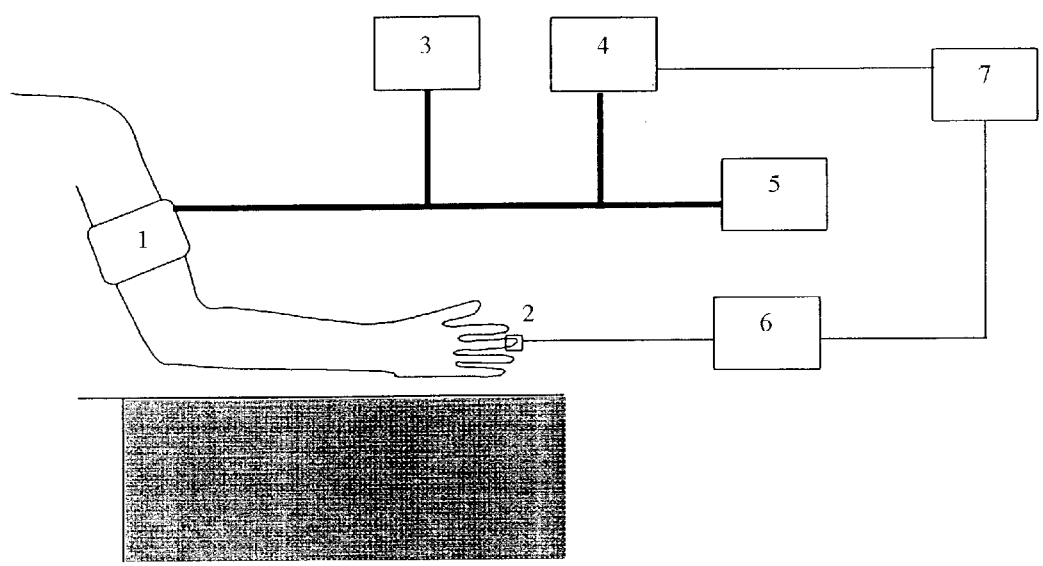
FIG. 1 is a schematic illustration of a system for the measurement of the SBP using a pressure cuff and a PPG sensor.
Figure 2:
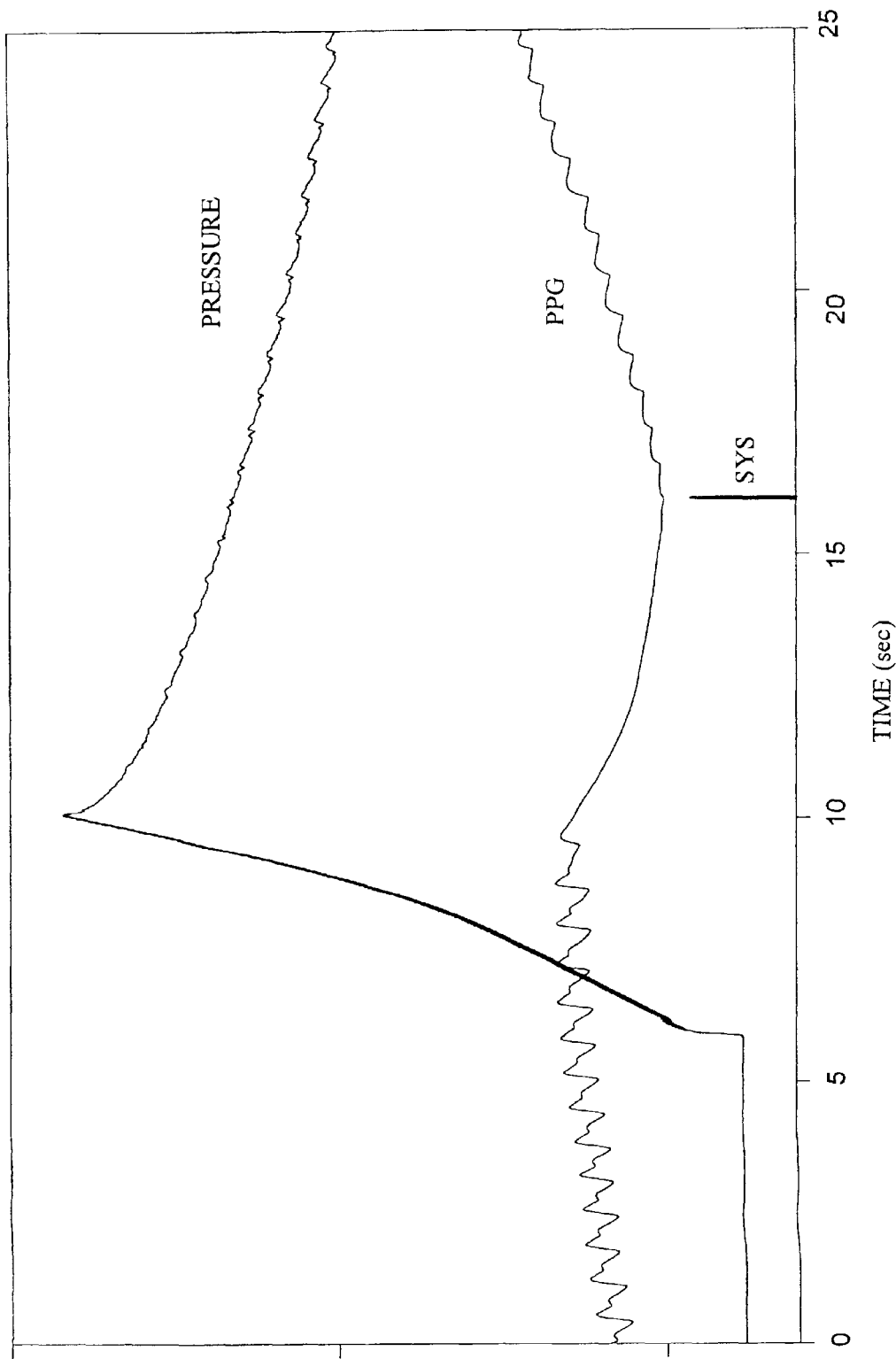
FIG. 2 is a typical example of the curve of cuff pressure and PPG signal against time illustrating the underlying principle of SBP measurement using a pressure cuff and a PPG sensor.
Figure 3:
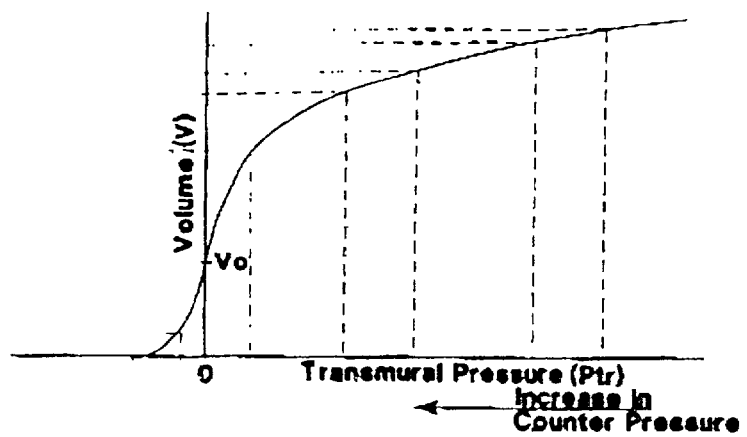
FIG. 3 is a plot of the blood volume in an artery as a function of the transmural blood pressure.

Referring now to the drawings, it should be noted that certain implementations of the method of the present invention may be achieved using the structural elements already described above with reference to FIG. 1. Thus, in general terms, the method includes: generating a first signal indicative of cardiac induced pulsatile variations in tissue blood volume in a first region of the subject's body; applying a pressure cuff to a second region of the subject's body proximal with respect to the first region; increasing a pressure within the pressure cuff to a pressure sufficient to prevent sensing of cardiac induced pulsatile variations in tissue blood volume in the first region; reducing a pressure within the pressure cuff; and identifying as a systolic blood pressure of the subject a cuff pressure at which the cardiac induced pulsatile variations in tissue blood volume in the first region are found to restart.

The main feature which distinguishes the method of the present invention from prior art techniques for SBP measurement based on pressure cuff and PPG is the manner in which the cuff pressure is raised. Specifically, as explained above, it is a particular feature of the method of the present invention that the cuff pressure is raised in such a manner that two conditions will be satisfied: (1) The cuff air pressure takes sufficient time to reach the SBP value to avoid blood pressure in the arteries under the PPG sensor being too low, thereby avoiding collapse of the arterioles under the PPG sensor; and (2) The increase of the cuff air pressure between the DBP value and the SBP value is not overly slow in a manner which would cause a relatively high mean blood pressure in the arteries distal to the cuff, and could lead to reduced sensitivity in detecting the restart of blood flow when the cuff air pressure decreases to just below SBP value.

Figure 4A:
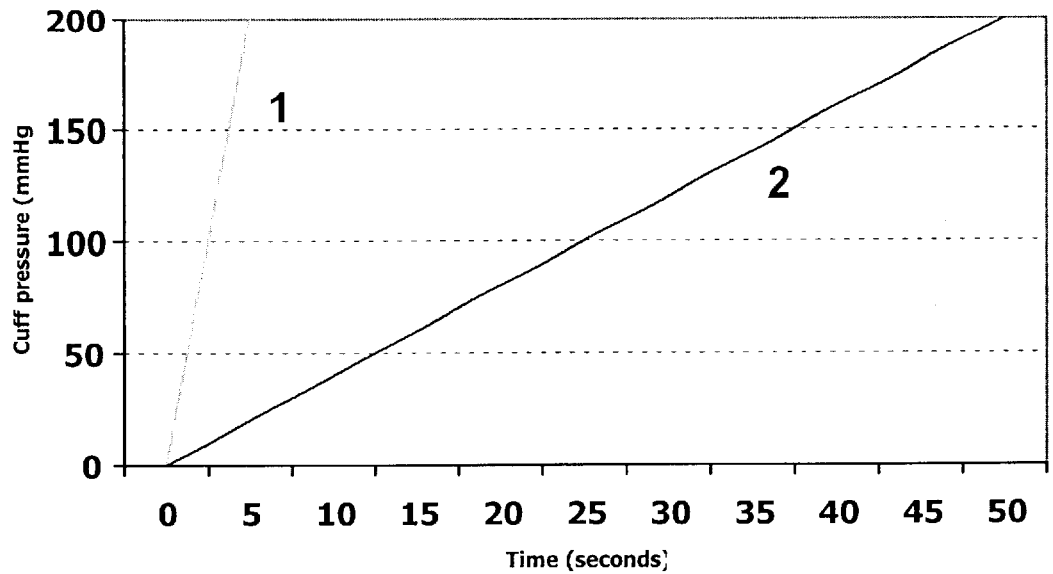
FIG. 4A is a plot of cuff pressure against time illustrating the conventional approaches to increasing cuff pressure for SBP measurement.
Figure 4A:
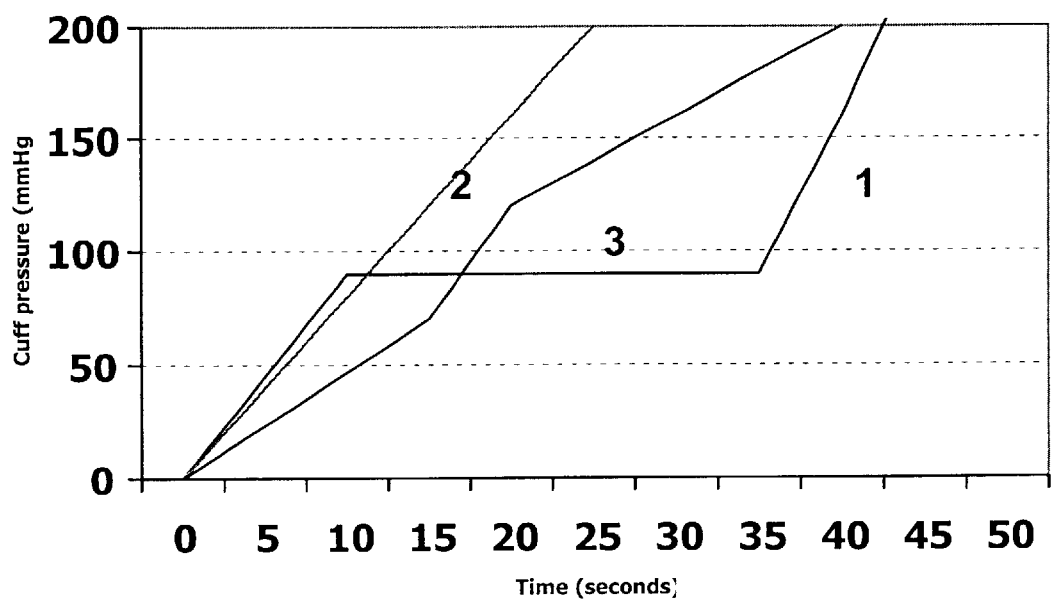

It will immediately be appreciated that the sequences of pressure increase of the present invention stand in clear contrast to the conventional techniques employed as illustrated in FIG. 4A. Specifically, the common practice is to raise the cuff pressure to above the SBP in no more than a few seconds. This results in almost immediate occlusion of the arteries under the cuff. Consequently, the blood volume is rapidly redistributed, flowing from the arteries (higher pressure) to the unstretched veins, resulting in reduction of the blood pressure in the arteries. This allows, at least in some cases, collapse of the blood vessels under the PPG sensor which is thought to be responsible for the unreliable measurement of SBP.

Similarly, the sequences of pressure increase of the present invention stand in clear contrast to the teachings of the aforementioned Blazek et al. patent in which pressure is increased at a uniform rate of about 4 mmHg/s. This slow increase, particularly over the range between the diastolic and systolic blood pressures, leads to increased distention of the blood vessels with the consequent PPG signal impairment mentioned above.

By way of non-limiting examples, three particular examples of preferred sequences of cuff pressure increase will now be described with reference to FIG. 4B.

EXAMPLE 1

This first example is based on pressure-limited venous occlusion. When a constant cuff pressure below SBP value is applied to the arm, the veins under the cuff collapse and are closed, and venous blood pressure within the arm increases. When the venous blood pressure reaches the cuff air pressure, the veins re-open such that the venous blood pressure cannot exceed the applied cuff pressure. As a result, so long as the applied cuff pressure does not exceed significantly the value of DBP, the cuff pressure may be maintained for long periods without causing over-distension of the blood vessels. The required increase of the cuff air pressure to above the SBP is then performed by raising the applied cuff pressure relatively rapidly.

In quantitative terms, this example may be defined as a two stage process: in the first stage, the pressure within the pressure cuff is increased in a manner such that it takes at least 10 seconds for the cuff pressure to reach 100 mmHg; in the second stage, the pressure is raised rapidly such that the average rate of increase between 100 mmHg and 160 mmHg is at least 20 mmHg per second. In a particularly convenient implementation, a pause of at least about 10 seconds at a constant pressure, typically in the range from about 40 to about 100 mmHg and most preferably in the range from 40 mmHg to 60 mmHg, may be introduced into an otherwise rapid pressure increase.

EXAMPLE 2

According to a second example, the pressure within the pressure cuff is increased at a substantially constant rate chosen to allow the required degree of accumulation of blood within the blood vessels. Preferably, this rate is chosen such that it takes at between 10 and 30 seconds for the cuff pressure to reach 160 mmHg. Most preferably, the rate of cuff pressure increase is chosen to be between about 8 and about 12 mmHg/s.

EXAMPLE 3

Clearly, the examples described thus far have been chosen based upon certain assumptions as to the "normal" ranges within which the DBP and SBP of subjects can, in most cases, be expected to fall. In certain extreme cases, slight adaptations or extensions of the pressure increase sequence might be required.

The third example presents an improvement to this approach in which the rate of increase in applied cuff pressure is changed as a function of a physiological measurement which is itself indicative of the proximity of the applied pressure to the DBP and SBP.

Figure 5:
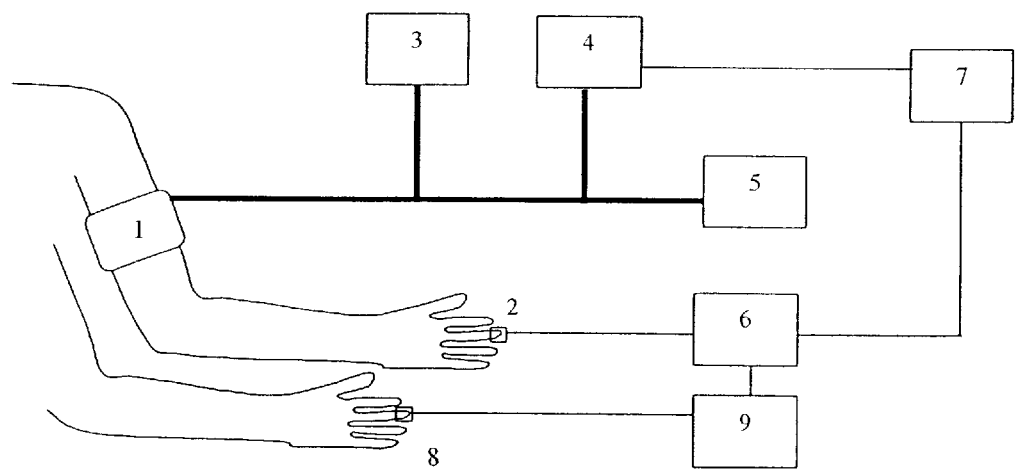
FIG. 5 is a schematic illustration of a system, constructed and operative according to the teachings of the present invention, for performing arterial blood pressure measurements according to a preferred implementation of the present invention.
Figure 6:
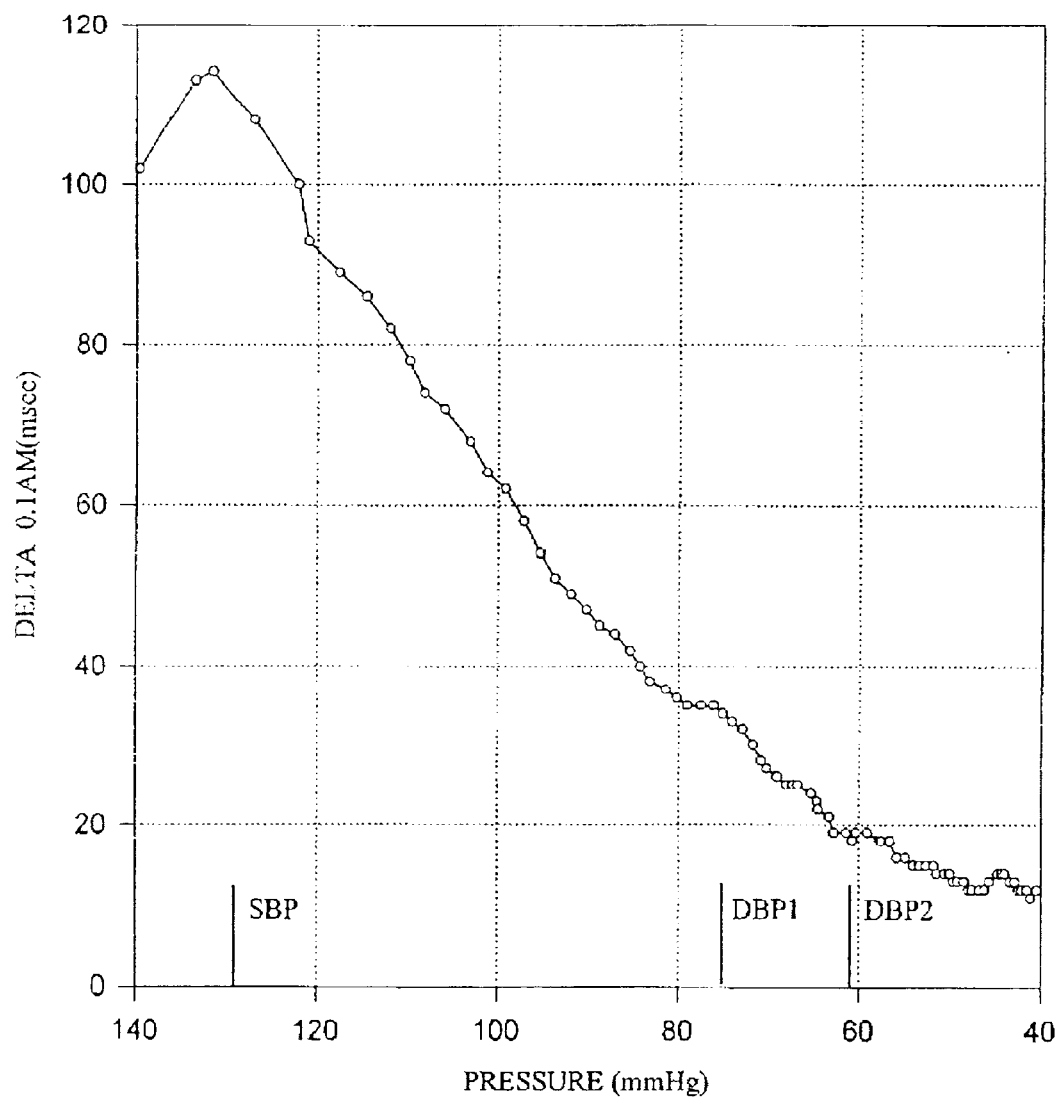
FIG. 6 is a plot showing the relationship between cuff pressure and the resulting delay between two PPG signals obtained using the system of FIG. 5 for a particular subject.

Specifically, with reference to FIGS. 5 and 6, this example is based upon a device and method disclosed in co-pending U.S. patent application Ser. No. 09/328,406 filed Jun. 9, 1999, which is hereby incorporated by reference as if fully set out herein. The device (FIG. 5) is generally similar to that of FIG. 1, but adds a second PPG sensor 8 with its associated electronics 9.

The signals from sensors 2 and 8 are indicative of cardiac induced pulsatile variations in tissue blood volume within the respective fingers of the subject's body. These signals are processed by computer 7 to derive values of a delay A between pulses in the signal from sensor 8 and corresponding pulses in the signal from sensor 2. The delay is preferably derived as a corrected value by evaluating a baseline value of the delay when the variable cuff air pressure is substantially zero and calculating a corrected delay by deduction of the baseline value from measurements of the delay.

When the pressure applied to the cuff 1 is varied, the corrected delay Δ is found to vary in a manner such that the DBP and SBP fall within predefined ranges of values of Δ. A typical example of the variation of Δ with applied cuff pressure is shown in FIG. 6.

Based on these observations, the third example of a sequence of pressure increase according to the teachings of the present invention raises the applied cuff pressure at a rate which changes as a function of the delay Δ until the first signal no longer provides identifiable pulses corresponding to cardiac induced pulsatile variations in tissue blood volume. In this way, the changing of the rate of pressure increase is inherently personalized to the appropriate pressure ranges for each individual subject.

In a particularly preferred implementation, the rate of pressure increase is chosen to be relatively slow for values of delay Δ in the region of the DBP and/or SBP, while being relatively rapid for intermediate values of delay Δ. This provides an additional possibility of measuring PPG signals for evaluation of the DBP and/or SBP during raising of the cuff air pressure. These measurements may be used alone, or in addition to the measurements taken during reduction of the applied air pressure.

In quantitative terms, the rate of pressure increase is preferably set at approximately 2 mmHg per second for values of the corrected delay below about 50 ms, at a value of at least about 5 mmHg per second for values of the corrected delay between about 50 and about 100 ms, and at approximately 2 mmHg per second for values of the corrected delay in excess of about 100 ms.

The boundary value of applied cuff pressure below which the signal from sensor 2 includes identifiable pulses corresponding to cardiac induced pulsatile variations in tissue blood volume may be identified during the raising of the applied cuff pressure, lowering of the pressure, or both.

In addition to the various sequences for increasing the applied cuff pressure, the present invention also provides features which make up an improved technique for reliably identifying the restarting of signal pulses corresponding to cardiac induced pulsatile variations in tissue blood volume.

Specifically, according to preferred implementations of the present invention, a pulse is identified as corresponding to cardiac induced pulsatile variations in tissue blood volume if it satisfies various criteria. Various criteria may be used, examples of which include, but are not limited to: having at least a minimum required area; having at least a certain value of maximum gradient; and falling within a given time delay after an independent reference signal indicative of cardiac pulse timing. In preferred implementations, the suspected pulse must be confirmed by satisfying at least two, and most preferably at least three, predefined criteria.

By way of a specific preferred example, a processing algorithm may be constructed as follows:

Ten PPG pulses are determined from the light transmission curve before the air pressure application, by detecting the pulses minima. Then the initial (baseline) area and the initial (baseline) maximal derivative are derived for each pulse, and from them the average initial (baseline) area $A_0$ and the average initial (baseline) maximal derivative $D_0$ are derived.

Then the cuff is inflated and deflated, and during the deflation we detect the minima in the light transmission curve of the affected hand. Three parameters are then calculated for the curve between two successive minima: the area A between the minima, the maximal derivative, $D_{aff}$, immediately after the first minimum, $M_{aff}$, and the time delay TD between the minimum in the affected hand, $M_{aff}$, and the minimum in the corresponding pulse in the non-affected hand.

The criteria for accepting that curve between the two minima as a PPG pulse are:

$A > 0.01\ A_0, D_{aff} > 0.01 D_0$, 100 ms < TD < 250 ms.

If the curve between the two minima satisfies these conditions, and the same is true for the regions between the next 10 minima, then the curve between the two first minima is accepted as a PPG pulse. That means that the air pressure, which corresponds to that pulse is the SBP.

According to a further preferred implementation, the condition on TD may be based on an approximate relationship between values of TD and the cuff pressure for the given patient derived empirically from measurements during the cuff pressure increase. The approximate relationship is preferably constructed as a polynomial of order between two and four fitted to the measurements taken, and most preferably, a third order polynomial is used.

It will be appreciated that the above descriptions are intended only to serve as examples, and that many other embodiments are possible within the spirit and the scope of the present invention.

What is claimed is:

1. A method for measuring systolic blood pressure in a subject, the method comprising:

(a) generating a first signal indicative of cardiac induced pulsatile variations in tissue blood volume in a first region of the subject's body;

(b) applying a pressure cuff to a second region of the subject's body proximal with respect to said first region;

(c) increasing a pressure within said pressure cuff to a pressure sufficient to prevent sensing of cardiac induced pulsatile variations in tissue blood volume in said first region;

(d) reducing a pressure within said pressure cuff; and (e) identifying as a systolic blood pressure of the subject a cuff pressure at which said cardiac induced pulsatile variations in tissue blood volume in said first region are found to restart, wherein said increasing of pressure within said pressure cuff is performed such that it takes at least 10 seconds for the cuff pressure to reach 100 mmHg, and such that the average rate of increase is at least 20 mmHg per second from 100 mmHg up to said pressure sufficient to prevent sensing of cardiac induced pulsatile variations.

2. The method of claim 1, wherein said identifying includes:

(a) integrating said first signal with respect to time over the length of a suspected pulse to derive an area under said pulse; and (b) identifying said suspected pulse as a restarting of cardiac induced pulsatile variations in tissue blood volume only if said area exceeds a given minimum value.

3. The method of claim 1, wherein said identifying includes:

(a) deriving a maximum gradient of said first signal with respect to time over the length of a suspected pulse; and (b) identifying said suspected pulse as a restarting of cardiac induced pulsatile variations in tissue blood volume only if said maximum gradient exceeds a given minimum value.

4. The method of claim 1, further comprising:

(a) generating a second signal indicative of cardiac induced pulsatile variations in a third region of the subject's body;

(b) calculating a delay between features of said first and said second signals indicative of corresponding cardiac induced pulsatile variations; and (c) evaluating a baseline value of said delay when said pressure within said pressure cuff is substantially zero, and calculating a corrected delay by deduction of said baseline value from measurements of said delay, wherein said identifying includes identifying a suspected pulse as a restarting of cardiac induced pulsatile variations in tissue blood volume only if the value of said delay is between 100–250 ms.

5. The method of claim 1, further comprising:

(a) generating a second signal indicative of cardiac induced pulsatile variations;

(b) deriving empirically an approximate relationship between values of a delay of said first signal after said second signal and said cuff pressure; and (c) identifying a suspected pulse as a restarting of cardiac induced pulsatile variations in tissue blood volume only if said suspected pulse occurs within a given time window after a pulse of said second signal, said given time window being derived from said approximate relationship evaluated at an expected value of systolic blood pressure.

6. A method for measuring systolic blood pressure in a subject, the method comprising:

(a) generating a first signal indicative of cardiac induced pulsatile variations in tissue blood volume in a first region of the subject's body;

(b) applying a pressure cuff to a second region of the subject's body proximal with respect to said first region;

(c) generating a second signal indicative of cardiac induced pulsatile variations in a third region of the subject's body;

(d) calculating a delay between features of said first and said second signals indicative of corresponding cardiac induced pulsatile variations;

(e) evaluating a baseline value of said delay when said pressure within said pressure cuff is substantially zero, and calculating a corrected delay by deduction of said baseline value from measurements of said delay;

(f) increasing a pressure within said pressure cuff to a pressure sufficient to prevent sensing of cardiac induced pulsatile variations in tissue blood volume in said first region;

(g) reducing a pressure within said pressure cuff; and (h) identifying as a systolic blood pressure of the subject a cuff pressure at which said cardiac induced pulsatile variations in tissue blood volume in said first region are found to restart, wherein said increasing of pressure within said pressure cuff is performed at a substantially constant rate chosen such that it takes at least between 10 and 30 seconds for the cuff pressure to reach 160 mmHg, and wherein said identifying includes identifying a suspected pulse a restarting of cardiac induced pulsatile variations in tissue blood volume only if the value of said delay is between 100–250 ms.

7. The method of claim 6, wherein said identifying includes:

(a) integrating said first signal with respect to time over the length of a suspected pulse to derive an area under said pulse; and (b) identifying said suspected pulse as a restarting of cardiac induced pulsatile variations in tissue blood volume only if said area exceeds a given minimum value.

8. A method for measuring systolic blood pressure in a subject, the method comprising:

(a) generating first and second signals indicative, respectively, of cardiac induced pulsatile variations in tissue blood volume in a first region and a second region of the subject's body;

(b) processing said first and second signals to derive values of a delay between pulses in said first signal and corresponding pulses in said second signal;

(c) applying a variable pressure to a third region of the subject's body proximal with respect to said first region so as to affect blood flow through at least one artery in said third region, said variable pressure being varied as a function of time, said first, said second and said third regions being chosen such that said delay varies as a function of said variable pressure;

(d) raising said variable pressure at a rate which changes as a function of said delay until said first signal no longer provides identifiable pulses corresponding to cardiac induced pulsatile variations in tissue blood volume; and (e) identifying as the arterial systolic blood pressure the value of said variable pressure corresponding to a boundary below which said first signal includes identifiable pulses corresponding to cardiac induced pulsatile variations in tissue blood volume.

9. The method of claim 8, further comprising evaluating a baseline value of said delay when said variable pressure is substantially zero, and calculating a corrected delay by deduction of said baseline value from measurements of said delay.

10. The method of claim 9, wherein said identifying includes identifying a suspected pulse as a cardiac induced pulsatile variation in tissue blood volume only if the value of said corrected delay is between 100–250 ms.

11. The method of claim 9, wherein said rate is approximately 2 mmHg per second at least for values of said corrected delay below about 50 ms.

12. The method of claim 11, wherein said rate is at least about 5 mmHg per second at least for values of said corrected delay between about 50 and about 100 ms.

13. The method of claim 12, wherein said rate is approximately 2 mmHg per second at least for values of said corrected delay in excess of about 100 ms.

14. The method of claim 8, wherein said boundary is identified during said raising of said variable pressure.

15. The method of claim 8, wherein said boundary is identified during a subsequent step of reducing said variable pressure.

16. The method of claim 8, wherein said identifying includes:

(a) integrating said first signal with respect to time over the length of a suspected pulse to derive an area under said pulse; and (b) identifying said suspected pulse as a cardiac induced pulsatile variation in tissue blood volume only if said area exceeds a given minimum value.

17. The method of claim 8, wherein said identifying includes:

(a) deriving a maximum gradient of said first signal with respect to time over the length of a suspected pulse; and (b) identifying said suspected pulse as a cardiac induced pulsatile variation in tissue blood volume only if said maximum gradient exceeds a given minimum value.

18. The method of claim 8, further comprising:

(a) deriving empirically an approximate relationship between values of said delay of said first signal after said second signal and said cuff pressure; and (b) identifying a suspected pulse as a cardiac induced pulsatile variation in tissue blood volume only if said suspected pulse occurs within a given time window after a pulse of said second signal, said given time window being derived from said approximate relationship evaluated at an expected value of systolic blood pressure.

19. A method for measuring systolic blood pressure in a subject, the method comprising:

(a) generating a first signal indicative of cardiac induced pulsatile variations in tissue blood volume in a first region of the subject's body;

(b) applying a pressure cuff to a second region of the subject's body proximal with respect to said first region;

(c) generating a second signal indicative of cardiac induced pulsatile variations;

(d) deriving empirically an approximate relationship between values of a delay of said first signal after said second signal and pressure within said pressure cuff;

(e) increasing a pressure within said pressure cuff to a pressure sufficient to prevent sensing of cardiac induced pulsatile variations in tissue blood volume in said first region;

(f) reducing a pressure within said pressure cuff; and (g) identifying as a systolic blood pressure of the subject a cuff pressure at which said cardiac induced pulsatile variations in tissue blood volume in said first region are found to restart, wherein said increasing of pressure within said pressure cuff is performed at a substantially constant rate chosen such that it takes at least between 10 and 30 seconds for the cuff pressure to reach 160 mmHg, and wherein a suspected pulse is identified as a restarting of cardiac induced pulsatile variations in tissue blood volume only if said suspected pulse occurs within a given time window after a pulse of said second signal, said given time window being derived from said approximate relationship evaluated at an expected value of systolic blood pressure.

* * * * *

UNITED STATES PATENT AND TRADEMARK OFFICE
CERTIFICATE OF CORRECTION

PATENT NO. : 6,402,696 B1
DATED : June 11, 2002
INVENTOR(S) : Nitzan et al.

It is certified that error appears in the above-identified patent and that said Letters Patent is hereby corrected as shown below:

<u>Column 12, line 1 through column 14, line 19,</u>
Delete claims 8-19 in their entirety and insert therefore the following claims:

8. The method of claim 6, wherein said identifying includes:

(a) deriving a maximum gradient of said first signal with respect to time over the length of a suspected pulse; and (b) identifying said suspected pulse as a restarting of cardiac induced pulsatile variations in tissue blood volume only if said maximum gradient exceeds a given minimum value.

9. A method for measuring systolic blood pressure in a subject, the method comprising:

(a) generating first and second signals indicative, respectively, of cardiac induced pulsatile variations in tissue blood volume in a first region and a second region of the subject's body;

(b) processing said first and second signals to derive values of a delay between pulses in said first signal and corresponding pulses in said second signal:

(c) applying a variable pressure to a third region of the subject's body proximal with respect to said first region so as to affect blood flow through at least one artery in said third region, said variable pressure being varied as a function of time, said first, said second and said third regions being chosen such that said delay varies as a function of said variable pressure;

(d) raising said variable pressure at a rate which changes as a function of said delay until said first signal no longer provides identifiable pulses corresponding to cardiac induced pulsatile variations in tissue blood volume; and (e) identifying as the arterial systolic blood pressure the value of said variable pressure corresponding to a boundary below which said first signal includes identifiable pulses corresponding to cardiac induced pulsatile variations in tissue blood volume.

UNITED STATES PATENT AND TRADEMARK OFFICE
CERTIFICATE OF CORRECTION

PATENT NO. : 6,402,696 B1
DATED : June 11, 2002
INVENTOR(S) : Nitzan et al.

It is certified that error appears in the above-identified patent and that said Letters Patent is hereby corrected as shown below:

10. The method of claim 9, further comprising evaluating a baseline value of said delay when said variable pressure is substantially zero, and calculating a corrected delay by deduction of said baseline value from measurements of said delay.

11. The method of claim 10, wherein said identifying includes identifying a suspected pulse as a cardiac induced pulsatile variation in tissue blood volume only if the value of said corrected delay is between 100-250 ms.

12. The method of claim 10, wherein said rate is approximately 2 mmHg per second at least for values of said corrected delay below about 50 ms.

13. The method of claim 12, wherein said rate is at least about 5 mmHg per second at least for values of said corrected delay between about 50 and about 100 ms.

14. The method of claim 13, wherein said rate is approximately 2 mmHg per second at least for values of said corrected delay in excess of about 100 ms.

15. The method of claim 9, wherein said boundary is identified during said raising of said variable pressure.

16. The method of claim 9, wherein said boundary is identified during, a subsequent step of reducing said variable pressure.

17. The method of claim 9, wherein said identifying includes:

(a) integrating said first signal with respect to time over the length of a suspected pulse to derive an area under said pulse; and (b) identifying said suspected pulse as a cardiac induced pulsatile variation in tissue blood volume only if said area exceeds a given minimum value.

18. The method of claim 9. wherein said identifying includes:

(a) deriving a maximum gradient of said first signal with respect to time over the length of a suspected pulse; and (b) identifying said suspected pulse as a cardiac induced pulsatile variation in tissue blood volume only if said maximum gradient exceeds a given minimum value.

UNITED STATES PATENT AND TRADEMARK OFFICE
CERTIFICATE OF CORRECTION

PATENT NO. : 6,402,696 B1
DATED : June 11, 2002
INVENTOR(S) : Nitzan et al.

It is certified that error appears in the above-identified patent and that said Letters Patent is hereby corrected as shown below:

19. The method of claim 9, further comprising:

(a) deriving empirically an approximate relationship between values of said delay of said first signal after said second signal and said cuff pressure; and (b) identifying a suspected pulse as a cardiac induced pulsatile variation in tissue blood volume only if said suspected pulse occurs within a given time window after a pulse of said second signal, said given time window being derived from said approximate relationship evaluated at an expected value of systolic blood pressure.

20. A method for measuring systolic blood pressure in a subject, the method comprising:

(a) generating a first signal indicative of cardiac induced pulsatile variations in tissue blood volume in a first region of the subject's body;

(b) applying a pressure cuff to a second region of the subject's body proximal with respect to said first region;

(c) generating a second signal indicative of cardiac induced pulsatile variations;

(d) deriving empirically an approximate relationship between values of a delay of said first signal after said second signal and pressure within said pressure cuff;

(e) increasing a pressure within said pressure cuff to a pressure sufficient to prevent sensing of cardiac induced pulsatile variations in tissue blood volume in said first region;

(f) reducing a pressure within said pressure cuff; and

UNITED STATES PATENT AND TRADEMARK OFFICE
CERTIFICATE OF CORRECTION

PATENT NO.     : 6,402,696 B1
DATED          : June 11, 2002
INVENTOR(S)    : Nitzan et al.

It is certified that error appears in the above-identified patent and that said Letters Patent is hereby corrected as shown below:

(g)   identifying as a systolic blood pressure of the subject a cuff pressure at which said cardiac induced pulsatile variations in tissue blood volume in said first region are found to restart, wherein said increasing of pressure within said pressure cuff is performed at a substantially constant rate chosen such that it takes at least between 10 and 30 seconds for the cuff pressure to reach 160 mmHg,
and wherein a suspected pulse is identified as a restarting of cardiac induced pulsatile variations in tissue blood volume only if said suspected pulse occurs within a given time window after a pulse of said second signal, said given time window being derived from said approximate relationship evaluated at an expected value of systolic blood pressure.

Signed and Sealed this

Nineteenth Day of November, 2002

*Attest:*

JAMES E. ROGAN
*Attesting Officer*     *Director of the United States Patent and Trademark Office*